United States Patent
Lee

(10) Patent No.: US 8,256,609 B1
(45) Date of Patent: Sep. 4, 2012

(54) DISPENSING SYSTEM

(75) Inventor: Budiman Lee, Chatsworth, CA (US)

(73) Assignee: Line One Laboratories Inc. (USA), Chatsworth, CA (US)

( * ) Notice: Subject to any disclaimer, the term of this patent is extended or adjusted under 35 U.S.C. 154(b) by 0 days.

(21) Appl. No.: 13/230,602

(22) Filed: Sep. 12, 2011

(51) Int. Cl.
*B65D 85/08* (2006.01)
(52) U.S. Cl. .......................... 206/69; 206/484
(58) Field of Classification Search .......... None
See application file for complete search history.

(56) References Cited

U.S. PATENT DOCUMENTS

| | | | | |
|---|---|---|---|---|
| 5,005,695 | A * | 4/1991 | Tennefos et al. | 206/69 |
| 6,742,521 | B2 * | 6/2004 | McCleskey et al. | 128/842 |
| 7,938,256 | B2 * | 5/2011 | Nikitczuk et al. | 206/69 |
| 2003/0141218 | A1 * | 7/2003 | Stephens et al. | 206/820 |
| 2005/0045497 | A1 * | 3/2005 | Sample | 206/69 |

* cited by examiner

*Primary Examiner* — Jacob K Ackun
(74) *Attorney, Agent, or Firm* — Sheldon Mak & Anderson

(57) ABSTRACT

A device comprising a sealed package having a front wall, a rear wall, a top edge, a bottom edge, a lubricant compartment and a prophylactic compartment, with the compartments proximate to each other. A lubricant is in the lubricant compartment and a prophylactic is in the prophylactic compartment.

11 Claims, 3 Drawing Sheets

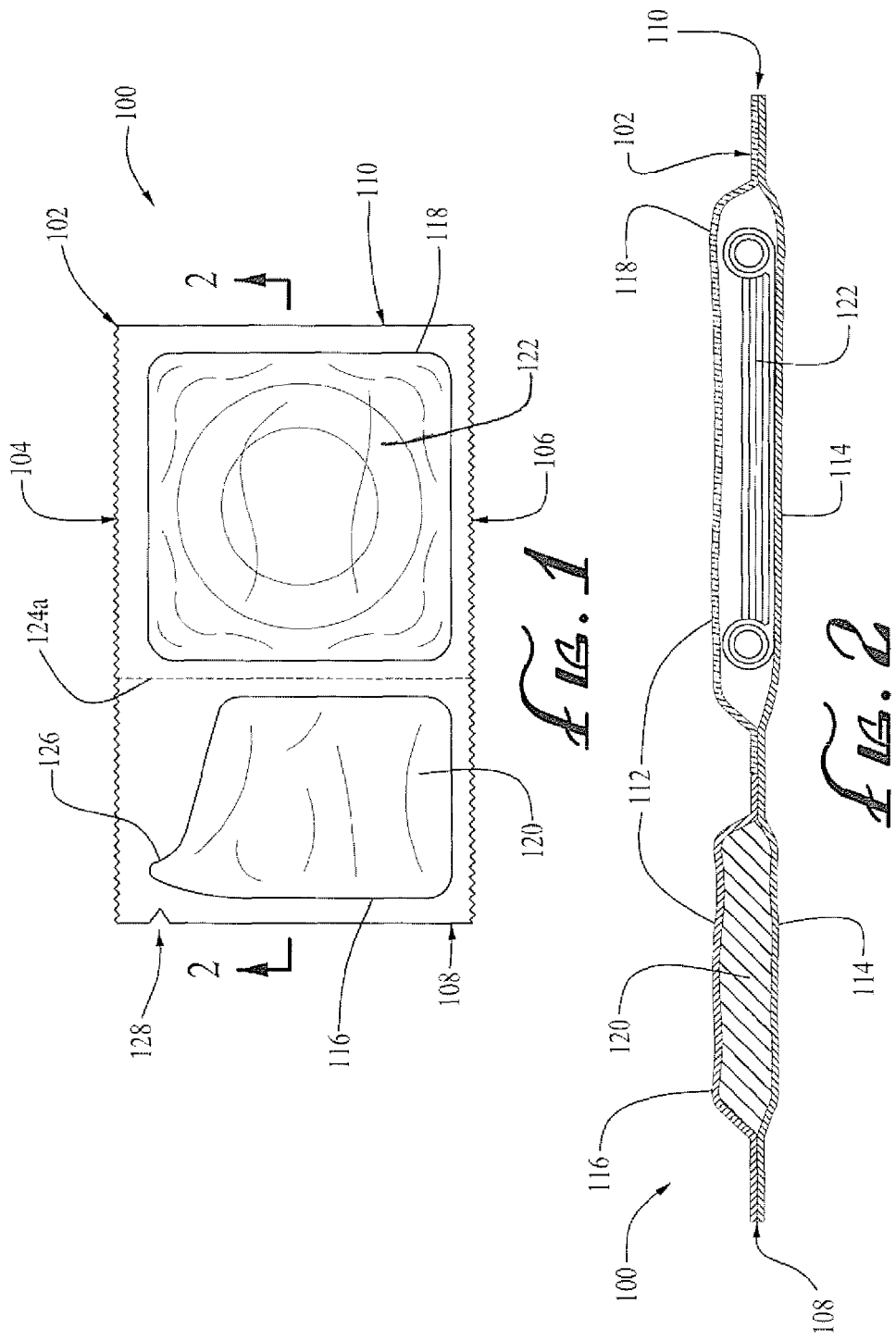

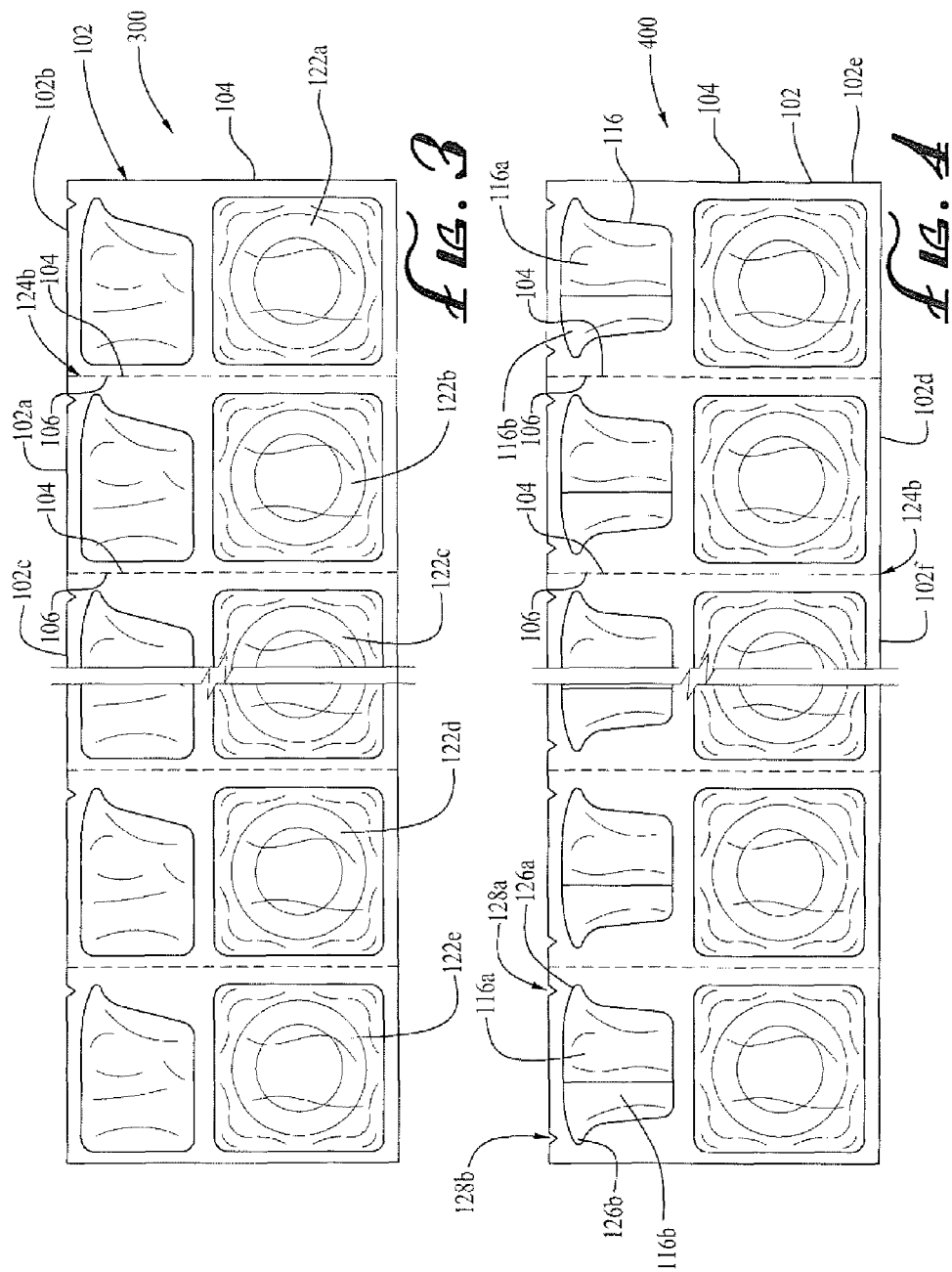

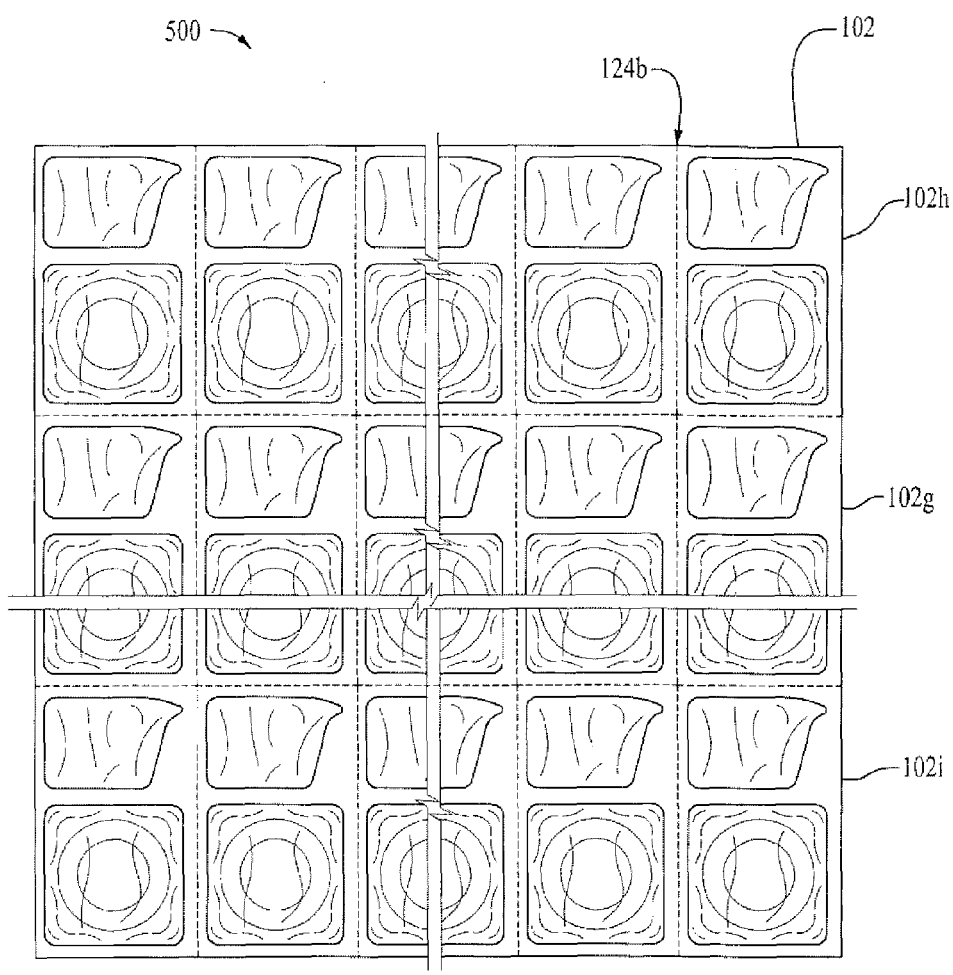

DISPENSING SYSTEM

BACKGROUND

Prophylactic and lubricants are commonly used during sex. Prophylactics are used for birth control and disease prevention purposes. Lubricants are commonly used for massages, and also for comfort, particularly with women past menopause.

Prophylactics are commonly dispensed through drugstores and through vending machines. Lubricants are commonly dispensed in containers containing much larger quantities of lubricant than needed at any single time, which is inconvenient to carry such as in a wallet, commonly used by men for carrying prophylactics. One exception to this is pre-lubricated prophylactics. A disadvantage of pre-lubricated prophylactics is that it is not possible to use the lubricant separately from the prophylactic, such as for massage or foreplay.

A problem associated with having separate dispensing systems for prophylactics and lubricants is that only one may be available when both are needed, and accessing those can be inconvenient and mood-destroying at the time of need.

Accordingly, there is a need for a better dispensing system for providing access to lubricant and prophylactics.

SUMMARY

The present invention is directed to such a dispensing system, and in particular, a device is provided in the form of a sealed package having a front wall, a rear wall, a lubricant compartment, and a prophylactic compartment. A lubricant is in the lubricant compartment and a prophylactic is in the prophylactic compartment. Thus both items are available in a single sealed package which can be provided and sold as a single unit, such as in dispensing machines.

Preferably, the lubricant compartment is trapezoidally shaped.

Preferably the front wall of the sealed package is substantially transparent so that users can easily view the contents of the package, and be sure to open the right compartment at the right time.

The front wall of the sealed package preferably is formed of burstable polyester film, with the rear wall of the sealed package substantially opaque, such as being formed of aluminum.

For access to the compartments of the sealed package so the compartments can be easily opened by hand without a tool, one or more weakened sections can be provided.

To control dispensing of the lubricant, preferably the lubricant compartment comprises a neck providing a narrow dispensing section. Optionally the lubricant compartment can have two or more sub-compartments, each having such a neck, and one of the sub-compartments can contain a germicide. So that one compartment can be separated from the other compartment, there can be perforations therebetween. Typically, the compartments are side by side, and can be adjoining.

In one form of the invention, a plurality of sealed packages are provided connected together in the form of a substantially rectangular sheet of a sufficient number so that at least one of the sealed packages is a mid package connected to at least two adjoining packages. For example, a mid package can be connected at its top edge to a first adjoining package at the bottom edge of the first adjoining package, and the mid package can be connected at its bottom edge to a second adjoining package at the top edge of the second adjoining package. Alternatively, the mid package can be connected at its first side edge to a first adjoining package at one of its side edges, and at its second side edge to a second adjoining package at one of the side edges of the second adjoining package.

In multipackage configurations, the sealed packages can be separated by perforations so that each sealed package can be stripped off one at a time.

Preferably the prophylactics are of different colors. This is particularly useful when different types or different sizes of prophylactics are provided, so that colors can be used for color coding.

DRAWINGS

These and other features, aspects and advantages of the present invention will become better understood with regard to the following description, appended claims, and accompanying figures where:

FIG. 1 is a front elevation view of a first version of a dispensing system according to the present invention comprising a sealed package;

FIG. 2 is a sectional view of the package of FIG. 1 taken along line 2-2 in FIG. 1;

FIG. 3 is a front elevation view of a second version of a dispensing system according to the present invention comprising a plurality of the sealed packages of FIG. 1 secured to each other;

FIG. 4 is a front elevation view of a third version of the invention; and

FIG. 5 is a front elevation view of a fourth version of the invention.

DESCRIPTION

Referring now to FIGS. 1 and 2, a dispensing system 100 according to the present invention comprises a sealed package 102 having a top edge 104, a bottom edge 106, a first side edge 108, a second side edge 110, a front wall 112, a rear wall 114, a lubricant compartment 116, and a prophylactic compartment 118. The top edge 104 and bottom edge 106 can be ridged, smooth, or any other shape. Either or both compartments 116, 118 can be burstable, i.e. able to be burst open by the application of external pressure by hand. Generally only the prophylactic compartment 118 is burstable.

The lubricant compartment 116 contains a lubricant 120, and the prophylactic compartment 118 contains a prophylactic 122. The thickness of the lubricant compartment 116 typically is about 0.1 inches when containing the lubricant 120, and the thickness of the prophylactic compartment typically is about 0.2 inches when containing the prophylactic 122. The prophylactic 122 can be a condom of any size, shape, or color, including but not limited to, lubricated, non-lubricated, ribbed, scented, flavored, or colored condoms. The lubricant compartment 116 can be located side-by-side with the prophylactic compartment 118 or in any other arrangement that allows both the lubricant compartment 116 and the prophylactic compartment 118 to fit without overlapping in the sealed package 102. There can be perforations 124a separating the lubricant compartment 116 from the prophylactic compartment 118 so that the lubricant compartment 116 can be stripped from the prophylactic compartment 118.

The lubricant compartment 116 can be trapezoidally shaped and preferably can comprise a neck 126. The neck 126 facilitates the dispensing of the lubricant 120 from the lubricant compartment 116 by funneling the lubricant 120 through a focused opening. Preferably, the sealed package 102 comprises a weakened section 128 for opening the lubricant compartment 116. The weakened section 128 can be comprised of, but not limited to, a slit, a "V"-shaped indentation, or a small perforation. The weakened section 128 can be located near the neck 126 of the lubricant compartment 116 such that the neck 126 is exposed when the sealed package 102 is torn at the weakened section 128, or can be located anywhere on the sealed package 102 that facilitates dispensing of the lubricant 120.

Preferably the front wall 112 is substantially transparent and is comprised of, but not limited to, a burstable polyester film, a plastic covering, or any other substantially transparent, flexible, polymeric material. A substantially transparent material is desirable because the contents of the sealed package 102 can be seen without having to open it. It is also desirable that the front wall 112 be sufficiently thin, i.e. sufficiently small in thickness, that it is burstable by hand. For example, the front wall 112 can be about 0.004 inches thick. Preferably the rear wall 114 can be substantially opaque and is comprised of, but not limited to, aluminum, paper, or any other opaque material. The rear wall 114 can be about 0.006 inches thick. An opaque material is desirable so that markings on the sealed package 102 can be seen. Both the front wall 112 and the rear wall 114 can comprise markings. Additionally, both the front wall 112 and rear wall 114 can be transparent, and both the front wall 112 and rear wall 114 can be opaque, or the front wall 112 can be transparent and the rear wall 114 can be opaque and vice versa.

The top edge 104 and bottom edge 106 are shown in FIG. 1 as having broken perforations that can results when the package 102 is separated from another package, as is possible in the versions shown in FIGS. 1-3. However, this is optional, and when the packages 102 are produced as single discrete units, typically there are no perforations.

Referring now to FIG. 3, a dispensing system 300 comprising a plurality of the sealed packages 102 connected together in the form of a substantially rectangular sheet. The term "rectangular" includes "square." The sealed packages 102 are proximate to each other such that there is a mid package 102*a* connected at its top edge 104 to a first adjoining package 102*b* at the bottom edge 106 of the first adjoining package 102*b*, and at its bottom edge 106 to a second adjoining package 102*c* at the top edge 106 of the second adjoining package 102*c*. Any of the sealed packages 102 can serve as a mid package 102*a* and/or an adjoining package 102*b*, 102*c*. The sealed packages 102 are separated by perforations 124*b* so that each sealed package 102 can be removed from the sheet one at a time or in a group of more than one package 102.

Optionally, different colored prophylactics 122*a*, 122*b*, 122*c*, 122*d*, 122*e* can be used. For example, prophylactic 122*a* can be green, prophylactic 122*b* can be yellow, prophylactic 122*c* can be purple, prophylactic 122*d* can be blue, and prophylactic 122*e* can be orange. Additionally, the prophylactics 122*a*, 122*b*, 122*c*, 122*d*, 122*e* can be a condom of any size, shape, or color, including but not limited to, lubricated, non-lubricated, ribbed, scented, flavored, or colored condoms. Different colors can be used for coding different types of condoms, such as by size, lubricant or no lubricant, thickness, scent, and/or ribs.

Referring now to FIG. 4, a dispensing system 400 comprising a plurality of the sealed packages 102 connected together in the form of a substantially rectangular sheet. The term "rectangular" includes "square." The sealed packages 102 are proximate to each other such that there is a mid package 102*d* connected at its top edge 104 to a first adjoining package 102*e* at the bottom edge 106 of the first adjoining package 102*e*, and at its bottom edge 106 to a second adjoining package 102*f* at the top edge 106 of the second adjoining package 102*f*. Any of the sealed packages 102 can serve as a mid package 102*d* and/or an adjoining package 102*e*, 102*f*. The sealed packages 102 are separated by perforations 124*b* so that each sealed package 102 can be stripped off one at a time.

The lubricant compartment 116 optionally comprises at least two sub-compartments 116*a*, 116*b*, with each sub-compartment 116*a*, 116*b* comprising a neck 126*a*, 126*b*. One of the sub-compartments 116*b* optionally contains a germicide. In other versions, the sub-compartments 116*a*, 116*b* can contain various liquids or gels, including, but not limited to, spermicide, massage oil, flavored liquid, or scented liquid. Therefore, it is understood that the term "lubricant compartment" means that various other liquids and/or gels can be contained within the compartment in addition to lubricant. Additionally, the sealed packages 102 can comprise weakened sections 128*a*, 128*b* for opening the sub-compartments 116*a*, 116*b*. The weakened sections 128*a*, 128*b* can be comprised of, but not limited to, a slit, a "V"-shaped indentation, or a small perforation. The weakened sections 128*a*, 128*b* can be located near the necks 126*a*, 126*b* of the sub-compartments 116*a*, 116*b* such that the necks 126*a*, 126*b* are exposed when the sealed packages 102 are torn at the weakened sections 128*a*, 128*b*, or can be located anywhere on the sealed packages 102 that facilitates dispensing of the contents of the sub-compartments 116*a*, 116*b*.

Referring now to FIG. 5, a system 500 comprising a plurality of sealed packages 102 connected together in the form of a substantially rectangular sheet. The term "rectangular" includes "square." The sealed packages 102 are proximate to each other such that there is a mid package connected to at least two adjoining packages. Any of the sealed packages 102 can serve as a mid package and/or an adjoining package. The sealed packages 102 are separated by perforations 124*b* so that each sealed package 102 can be stripped off one at a time.

In another version of the invention, the sealed packages 102 are proximate to each other such that there is a mid package 102*g* connected at its first side edge 108 to a first adjoining package 102*h* at one of the side edges of the first adjoining package 102*h*, and at its second side edge 110 to a second adjoining package 102*i* at one of the side edges of the second adjoining package 102*i*.

Although the present invention has been discussed in considerable detail with reference to certain preferred embodiments, other embodiments are possible. For example, the front wall 112 may be comprised of multiple different layers, or the sealed package of FIG. 1 can be packaged back-to-back. Therefore, the scope of the appended claims should not be limited to the description of preferred embodiments contained in this disclosure.

All the features disclosed in this specification (including any accompanying claims, abstract, and drawings) can be replaced by alternative features serving the same, equivalent or similar purpose, unless each feature disclosed is one example only of a generic series of equivalent or similar features.

What is claimed is:

1. A device comprising:
   a) a plurality of sealed packages, each package comprising:
      i) a substantially transparent front wall formed of a burstable film;
      ii) a substantially opaque rear wall;
      iii) a top edge;
      iv) a bottom edge;
      v) a prophylactic compartment; and
      vi) a substantially trapezoidally shaped lubricant compartment not within the prophylactic compartment and having a neck for facilitating dispensing of the lubricant through a focused opening, wherein the prophylactic compartment is proximate to and side-by-side with the lubricant compartment;
b) weakened sections for opening each of the lubricant compartments;
c) lubricant in each of the lubricant compartments;
d) a prophylactic in each of the prophylactic compartments; and
e) wherein the packages are connected together in the form of a substantially rectangular sheet with perforations at the connection so each sealed package can be stripped off one at a time, the sheet having at least one package connected to two adjacent packages, a first connected package at the top edge, and a second connected package at the bottom edge.

2. A device comprising:
a) a plurality of sealed packages, each package comprising:
  i) a substantially transparent front wall formed of a burstable film;
  ii) a substantially opaque rear wall;
  iii) a top edge;
  iv) a bottom edge;
  v) a first side edge;
  vi) a second side edge;
  vii) a prophylactic compartment; and
  viii) a substantially trapezoidally shaped lubricant compartment not within the prophylactic compartment and having a neck for facilitating dispensing of the lubricant through a focused opening, wherein the prophylactic compartment is proximate to and side-by-side with the lubricant compartment;
b) weakened sections for opening each of the lubricant compartments;
c) lubricant in each of the lubricant compartments;
d) a prophylactic in each of the prophylactic compartments; and
e) wherein the packages are connected together in the form of a substantially rectangular sheet with perforations at the connection so each sealed package can be stripped off one at a time, the sheet having at least one package connected to two adjacent packages, a first connected package at its first side edge to a first adjoining package at one of the side edges of the first adjoining package, and the first connected package at its second side edge to a second adjoining package at one of the side edges of the second adjoining package.

3. The device of claim 1 or 2 wherein the front wall of the sealed package comprises a burstable polyester film.

4. The device of claim 1 or 2 wherein the rear wall of the sealed package comprises aluminum.

5. The device of claim 1 or 2 wherein the lubricant compartment comprises at least two sub-compartments, each sub-compartment comprising a neck.

6. The device of claim 5 wherein one of the sub-compartments contains germicide.

7. The device of claim 1 or 2 wherein perforations separate the lubricant compartment from the prophylactic compartment.

8. The device of claim 1 or 2 wherein at least two of the prophylactics are of different color.

9. The device of claim 1 or 2 wherein the lubricant compartments comprise at least two sub-compartments, each sub-compartment containing a different substance.

10. The device of claim 1 or 2 wherein perforations separate the lubricant compartments from the prophylactic compartments.

11. The device of claim 1 or 2 wherein the prophylactic is lubricated.

* * * * *